US009475698B2

(12) United States Patent
Heilmann et al.

(10) Patent No.: US 9,475,698 B2
(45) Date of Patent: Oct. 25, 2016

(54) HYDROTHERMAL CARBONIZATION OF SEWAGE WASTES

(71) Applicant: REGENTS OF THE UNIVERSITY OF MINNESOTA, Minneapolis, MN (US)

(72) Inventors: Steven M. Heilmann, Afton, MN (US); Frederick J. Schendel, Oakdale, MN (US); Marc Gregor Von Keitz, Minneapolis, MN (US); Kenneth J. Valentas, Golden Valley, MN (US); Anthony L. Mikula, Shell Lake, WI (US); Brandon Michael Wood, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 14/406,955

(22) PCT Filed: Mar. 8, 2013

(86) PCT No.: PCT/US2013/029842
§ 371 (c)(1),
(2) Date: Dec. 10, 2014

(87) PCT Pub. No.: WO2013/187955
PCT Pub. Date: Dec. 19, 2013

(65) Prior Publication Data
US 2015/0183641 A1 Jul. 2, 2015

Related U.S. Application Data

(60) Provisional application No. 61/660,282, filed on Jun. 15, 2012.

(51) Int. Cl.
C05F 7/00 (2006.01)
C05B 17/00 (2006.01)
(Continued)

(52) U.S. Cl.
CPC ............ *C01B 25/375* (2013.01); *C01B 25/22* (2013.01); *C01B 25/265* (2013.01); *C01B 25/32* (2013.01);
(Continued)

(58) Field of Classification Search
CPC ....... C05F 7/00; C05B 17/00; C01B 25/324; C01B 25/34; C01B 25/36; C01B 25/2216; C01B 25/22; C01B 25/375; C01B 25/265; C01B 25/37
USPC ............................................................ 71/12
See application file for complete search history.

(56) References Cited

U.S. PATENT DOCUMENTS

| 2011/0056124 A1 | 3/2011 | Heilmann et al. |
| 2011/0179981 A1 | 7/2011 | Van Naarden et al. |

(Continued)

FOREIGN PATENT DOCUMENTS

| JP | 2012024696 A | 2/2012 |
| WO | 2010/130589 A1 | 11/2010 |
| WO | 2011/143380 A2 | 11/2011 |

OTHER PUBLICATIONS

Everett, "Dewatering Wastewater Sludge by Heat Treatment," *Journal (Water Pollution Control Federation)*, Jan. 1972; 44(1):92-100.

(Continued)

*Primary Examiner* — Wayne Langel
(74) *Attorney, Agent, or Firm* — Mueting, Raasch & Gebhardt, PA

(57) ABSTRACT

The present disclosure provides methods for hydrothermally treating sewage wastes to preferably obtain valuable products, including fatty acids, carbon-neutral combustible hydrochar fuels, heavy metal salts for recycling into industrially important metals, and phosphoric acid and derivatives thereof. Fatty acids can be chemically transformed into useful products such as soaps, cosmetics and liquid transportation fuels such as biodiesel and conventional gasoline, diesel and aviation fuels; hydrochars created in the process can be combusted and the energy created used to generate electricity; heavy metal salts can be chemically reduced to form industrially important metals for use as catalysts; and phosphoric acid and its derivatives have very important roles as fertilizers in agriculture.

33 Claims, 3 Drawing Sheets

(51) Int. Cl.

| | |
|---|---|
| *C01B 25/26* | (2006.01) |
| *C01B 25/37* | (2006.01) |
| *C01B 25/22* | (2006.01) |
| *C01B 25/32* | (2006.01) |
| *C01B 25/34* | (2006.01) |
| *C01B 25/36* | (2006.01) |
| *C10L 5/44* | (2006.01) |
| *C10L 5/46* | (2006.01) |
| *C10L 9/08* | (2006.01) |
| *C02F 9/00* | (2006.01) |
| *C07C 67/56* | (2006.01) |
| *C02F 1/02* | (2006.01) |
| *C02F 1/26* | (2006.01) |
| *C02F 1/42* | (2006.01) |
| *C02F 1/44* | (2006.01) |
| *C02F 3/28* | (2006.01) |
| *C02F 101/10* | (2006.01) |
| *C02F 101/20* | (2006.01) |
| *C02F 101/22* | (2006.01) |
| *C02F 103/20* | (2006.01) |
| *C02F 1/52* | (2006.01) |

(52) U.S. Cl.
CPC ............. *C01B 25/324* (2013.01); *C01B 25/34* (2013.01); *C01B 25/36* (2013.01); *C01B 25/37* (2013.01); *C02F 9/00* (2013.01); *C05B 17/00* (2013.01); *C07C 67/56* (2013.01); *C10L 5/447* (2013.01); *C10L 5/46* (2013.01); *C10L 9/08* (2013.01); *C02F 1/025* (2013.01); *C02F 1/26* (2013.01); *C02F 1/42* (2013.01); *C02F 1/44* (2013.01); *C02F 1/52* (2013.01); *C02F 3/28* (2013.01); *C02F 2101/105* (2013.01); *C02F 2101/20* (2013.01); *C02F 2101/22* (2013.01); *C02F 2103/20* (2013.01); *C02F 2303/02* (2013.01); *C02F 2303/04* (2013.01); *C05F 7/00* (2013.01); *Y02E 50/10* (2013.01); *Y02E 50/30* (2013.01); *Y02T 50/678* (2013.01); *Y02W 10/37* (2015.05)

(56) References Cited

U.S. PATENT DOCUMENTS

| | | |
|---|---|---|
| 2011/0271588 A1 | 11/2011 | Schendel et al. |
| 2012/0103040 A1* | 5/2012 | Wolf .................. C10L 5/366 71/24 |

OTHER PUBLICATIONS

Libra, "Hydrothermal carbonization of biomass residuals: a comparative review of the chemistry, processes and applications of wet and dry pyrolysis," *Biofuels*, Jan. 2011; 2(1):89-124.

International Search Report and Written Opinion for PCT/US2013/029842 issued by the European Patent Office on Jul. 2, 2013; 9 pgs.

International Preliminary Report on Patentability for PCT/US2013/029842, mailed Dec. 24, 2014; 6 pgs.

Berge et al., "Hydrothermal carbonization of Municipal Waste Streams," *Environmental Science & Technology*, 2011:5696-5703.

Cao et al., "Chemical Structure of Swine-Manure Chars produced under Different Carbonization Conditions Investigated by Advanced Solid-State 13c Nuclear magnetic Resonance (NMR) Spectroscopy," *Energy &Fuels*, Jan. 20, 2011;25(1):388-397.

Heilmann et al., "Hydrothermal carbonization of microalgae II. Fatty acid, char, and algal nutrient products," *Applied Energy*, 2011;88(10):3286-3290.

Hultman and Lowen, "Combined Phosphorus Removal and Recovery," *Div of Water Resources Engineering, Royal Institute of Technology, S-100 44 Stockholm Sweden*; 2001, pgs. 11-18.

Karlsson, "Full Scale Plant Recovering Iron Phosphate at Helsingbor, Sweden," Proc $2^{nd}$ Int. Conference on recovery of Phosphates from Sewage and Agricultural Waste, CEEP, Holland Mar. 12-14, 2001.

Kepp et al., "Enhanced Stabilisation of Sewage Sludge through Thermal Hydrolysis—Three Years of Experience with Full Scale Plant" *Water Science & Technology*, 2000;42(9):89-96.

"Ohio Livestock Manure Management Guide" *The Ohio State University Extension*, Bulletin 604; Ed. James et al., Jan. 2006: 126 pgs.

Pettersson et al., "Leaching of ashes from co-combustion of sewage sludge and wood-Part I: Recovery of Phosphorous," *Science Direct*, 2008;32:224-235.

Singer and Mason, *The Ethics of What We Eat*, Rodale Books, Text Publishing Company, May 16, 2006, Cover page, publisher's page, and p. 43.

* cited by examiner

HYDROTHERMAL CARBONIZATION OF SEWAGE WASTES

This application is the U.S. National Stage of International Application No. PCT/US2013/029842, filed on Mar. 8, 2013, which claims the benefit of U.S. Provisional Application No. 61/660,282, filed Jun. 15, 2012, each of which is herein incorporated by reference in its entirety.

BACKGROUND

Our world is presently confronted with several very formidable problems, including an energy situation in which projections have been made of less than 50 remaining years of proven reserves of crude oil; increasing global temperatures that have resulted in glaciers melting and oceans rising, as well as severe climatic changes that seem to be accelerating in recent decades; and, perhaps the most foreboding problem of all, that known global reserves of phosphate rock are being rapidly depleted such that within a century global supplies will be exhausted. Phosphorus is an absolutely essential element for both plant and animal life, and the primary source of concentrated phosphorus is phosphate rock which is a non-renewable resource. Its depletion will have devastating effects, vastly reducing agricultural productivity and potentially causing massive global starvation of the projected 9.3 billion people that will inhabit the earth by 2050. Such predictions are reminiscent of those made concerning the global depletion of fixed nitrogen sources in the early 20th century. This problem was abated by the development of the Haber-Bosch process which converted diatomic nitrogen into ammonia. A parallel solution for phosphorus, however, does not exist, and recycling phosphorus from a variety of materials will be the only alternative. One further significant environmental problem associated with phosphorus is that since the end of World War II, massive quantities of phosphate have been applied to agricultural fields, golf courses, and lawns. Excess phosphate that is not incorporated into growing terrestrial plants eventually finds its way into rivers, lakes, aquifers and oceans. Under proper growing conditions, e.g., sunlight and nutrients including phosphate, microalgae can grow at very high rates, literally doubling their biomass in a matter of a few hours. They die and their decomposition consumes great quantities of oxygen resulting in fish kills and so-called "dead zones," even in very large bodies of water such as the Gulf of Mexico.

Since ancient times, manures have been utilized as fuels for heating and cooking as well as fertilizers for enriching agricultural soils. Obvious problems associated with such practices include the odious and odorous natures of these materials, as well as the presence of disease-causing pathogens. Prior to the mid 20th century, an additional very practical issue was the lack of large collection sites, with human sewages largely being discharged into private septic systems, and animal manures produced on relatively small family farms being disposed of by application back onto fields. Those situations have changed such that, with a growing urban population, municipal waste treatment facilities have become commonplace, and small family farms have given way to very large farms, often operated by corporations, that generally specialize in production of one domestic farm animal. As a result, confined animal feeding operations (CAFOs) have emerged that accrue very large quantities of animal manures. For the most part, these manures are currently applied back onto farm fields, but in an effort to circumvent environmental problems, the quantities applied are typically restricted by regulations that are intended to control levels of nitrogen and phosphorus nutrients. This has caused large farming operations to transport wet manures significant distances from the generating farm for application onto fields having greater latitudes in terms of nutrient restrictions. As well as causing very significant odor and disease problems for local populations in the vicinity the CAFO, manures have become very significant waste products having a negative commercial value to the CAFO producer.

Phosphorus levels in agricultural fertilizers have been characterized in phosphorus pentoxide equivalents, and values for several manures produced at CAFO and municipal waste processing facilities for operations within the United States are indicated in Table 1.

TABLE 1

Phosphorus capture potential for given animals per company/facility.

| Animal | Number of US Animals | $P_2O_5$ Equivalents per day in kg/animal | Herd Production Capacity per day (Kg) | Annual Production Capacity (Kg) |
|---|---|---|---|---|
| Feeding Pig | 50,000 | 0.068 | 3,400 | 1,241,000 |
| Dairy Cattle | 9,315 | 0.150 | 1,397 | 509,996 |
| Poultry (Laying Hens) | 12.9 million | 0.100 | 1.29 million | 470 million |
| Human & Municipal Wastes | 226.4 million | 0.291 | 65.9 million | 24.0 billion |

Consideration of whether phosphorus in sufficient quantity could be obtained from manure sources to alleviate a global shortage problem can be ascertained from the last entry in Table 1 of output from municipal waste treatment facilities. Phosphate rock has a phosphorus pentoxide equivalence of 0.33. At the present global annual application rate of 140 million metric tons of phosphate rock (46.2 million metric tons of phosphorus pentoxide), the output from the US municipal waste treatment facilities would provide 52% of the global requirement. The precise numbers of large swine, cattle, and poultry CAFOs are unknown, but conceivably an amount of phosphorus pentoxide equivalent to the amount from the municipal waste facilities could be obtained from those sources as well. Phosphoric acid has a phosphorus pentoxide equivalent of 0.70, with dehydrated derivatives being even higher. These materials can offer better volume efficiency for long term storage.

Therefore, there is an unmet need for technologies to sequester phosphorus in the near term for use in the future.

SUMMARY

In one aspect, the present disclosure provides a method of obtaining a phosphate from a sewage material. In one embodiment, the method includes: subjecting a wet sewage material (e.g., untreated sewage material) to a hydrothermal carbonization process to produce a hydrochar and an aqueous product stream; isolating the hydrochar (e.g., by filtration, centrifugation, or a combination thereof) from the aqueous product stream; treating at least a portion of the isolated hydrochar with an aqueous acid under conditions effective to provide an aqueous phosphate material; and isolating the acid-treated hydrochar (e.g., by filtration, centrifugation, or a combination thereof) from the aqueous phosphate material.

In another aspect, the present disclosure provides a method of obtaining fatty acid materials from a sewage material. In one embodiment, the method includes: subjecting a wet sewage material (e.g., untreated sewage material) to a hydrothermal carbonization process to produce a hydrochar and an aqueous product stream; isolating the hydrochar (e.g., by filtration, centrifugation, or a combination thereof) from the aqueous product stream; treating at least a portion of the isolated hydrochar with an organic solvent under conditions effective to extract the fatty acid materials into the organic solvent; and isolating the organic solvent-treated hydrochar (e.g., by filtration, centrifugation, or a combination thereof) from the organic solvent having the fatty acid materials therein. Optionally, the method further includes removing at least a portion of the organic solvent from the fatty acid materials. Optionally, the method further includes treating the isolated organic solvent-treated hydrochar with an aqueous acid under conditions effective to provide an aqueous phosphate material; and isolating the acid and organic solvent-treated hydrochar (e.g., by filtration, centrifugation, or a combination thereof) from the aqueous phosphate material.

In some embodiments, the method further includes combusting at least a portion of the isolated hydrochar and/or the isolated organic solvent-treated hydrochar to form an ash. In certain embodiments, at least a portion of the ash can be treated with an aqueous acid under conditions effective to provide an aqueous phosphate material and/or heavy metals.

In some embodiments the aqueous phosphate material provided can be suitable for use as a fertilizer or as a feedstock for anaerobic digestion without further processing. For embodiments in which the aqueous phosphate material includes heavy metals, optionally the methods can further include removing at least a portion of the heavy metals from the aqueous phosphate material. In some embodiments, the methods can further include removing at least a portion of the water (e.g., by evaporation, distillation, a membrane removal process such as crossflow filtration or dialysis separation, and combinations thereof) from the aqueous phosphate material to provide a dewatered phosphate material. In some embodiments, the dewatered phosphate material can be suitable for use with or without further processing as a fertilizer or used as a component in a variety of applications including, for example, foods, beverages, pharmaceuticals, personal care products, paints, cleaning products, ceramics, and flame retardant materials.

In certain embodiments, untreated and/or treated hydrochar can be suitable for use directly as carbon-neutral energy products or indirectly as energy pro-products. In some embodiments, hydrochars can be created that contain significantly increased levels of carbon content relative to starting sewage material and possess relatively high energy contents.

In certain embodiments, the aqueous product stream can be suitable for use as a fertilizer or an anaerobic digestion substrate without further processing. In some embodiments, carbonaceous solutes present in aqueous product streams of the invention can be subjected to microbial action and converted into methane as another energy product.

In certain embodiments of the methods disclosed herein, the wet sewage material (e.g., untreated sewage material) can include one or more of human wastes, dairy cattle manures, beef cattle manures, swine manures, poultry manures, and horse manures. Optionally water can be added to the wet sewage material to adjust the solids content. In certain embodiments, the wet sewage material has a solids content of 0.25% to 30% by weight. In certain embodiments, the wet sewage material has a cellulose content of less than 50% by weight.

Optionally, at least one multivalent cation (e.g., Al, Ca, Mg, Fe, or Zn) can be added to the wet sewage material (e.g., untreated sewage material) prior to hydrothermal carbonization. In certain embodiments, 0.1% to 10% by weight of the at least one multivalent cation can be added to the wet sewage material, based on the total dry solids content of the sewage material, which can provide a level of control for how much of the phosphate present in the system will be sorbed onto the hydrochar.

In certain embodiments, the temperature of the hydrothermal carbonization process can be 185° C. to 225° C. In certain embodiments, the time of the hydrothermal carbonization process can be 0.25 hours to 2 hours. In certain embodiments, the pressure of the hydrothermal carbonization process can be 10 to 26 atmospheres. In certain embodiments, the initial pH of the wet sewage material in the hydrothermal carbonization process can be 4 to 8.

Advantageously, in some embodiments, the methods disclosed herein can transform sewage sludges from odious and odorous materials into pathogen-free and much less odorous mixtures of materials having commercial value. Further, in some embodiments, the methods disclosed herein can abate the effects of global depletion of concentrated sources of phosphate such as phosphate rock by recovering phosphate from manures and sewages. Further, in some embodiments, the methods disclosed herein can reduce or minimize the effects of phosphate runoff from lawns and agricultural fields that contributes to eutrification, development of hypoxic conditions, and creation of dead zones in surface waters.

The above brief description of various embodiments of the present invention is not intended to describe each embodiment or every implementation of the present invention. Rather, a more complete understanding of the invention will become apparent and appreciated by reference to the following description and claims in view of the accompanying drawings. Further, it is to be understood that other embodiments may be utilized and structural changes may be made without departing from the scope of the present invention.

Definitions

As used herein, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

As used herein, "fatty acids and derivatives" mean compounds obtained by hydrolysis of fatty acid ester groups present in the sewage biomass that include fatty acids, monoacyl- and diacylglycerides.

As used herein, "hydrothermal carbonization" and "thermal hydrolysis" mean a process in which biomass and/or organic compounds are heated in water in a confined system. Hydrothermal carbonization (abbreviated as HTC) is differentiated from "liquefaction" and "gasification" processes that are conducted at substantially higher temperatures and pressures. For purposes of this invention, HTC processes are conducted from 185 to 225° C.

As used herein, "heavy metals" generally mean so-called transition metals such as nickel, lead, copper, zinc, chromium, cadmium and mercury.

As used herein, "hydrochar" means the insoluble product of a HTC process.

As used herein, "multivalent cationic metals" mean those metals that are not regarded as having significant negative environmental impact and include aluminum, calcium, magnesium, iron, and zinc. A level of insolubility of the corresponding phosphate salt is defined as having a solubility product constant (Ksp) of less than $10^{-5}$. In some embodiments the Ksp is less than $10^{-8}$, in certain embodiments less than $10^{-15}$, and in other certain embodiments less than $10^{-35}$.

As used herein "phosphate material" is meant to include phosphoric acid and phosphoric acid derivatives and/or salts thereof. The term is also meant to include dehydrated forms of phosphoric acid such as polyphosphoric acid and phosphorus pentoxide.

As used herein, "sewage sludge" and "manures" mean a combination of feces, urine and possible water added thereto either at the generation site to clean the facility or added in the practice of the invention. All agricultural manures are believed to be useful substrates in the practice of the invention. Human sewages are also important substrates in the invention. These sewages from municipal treatment facilities also include phosphates from rainfall runoffs from streets, lawns, and golf courses. A wide variety of other products including foods, beverages, pharmaceuticals, personal care products, paints and cleaning products can also contribute to the phosphate content of municipal sewage wastes.

As used herein, "sorbed" or "sorption" means the process in which one substance takes up or holds another via absorption or adsorption.

DETAILED DESCRIPTION OF ILLUSTRATIVE EMBODIMENTS

Figure 1:
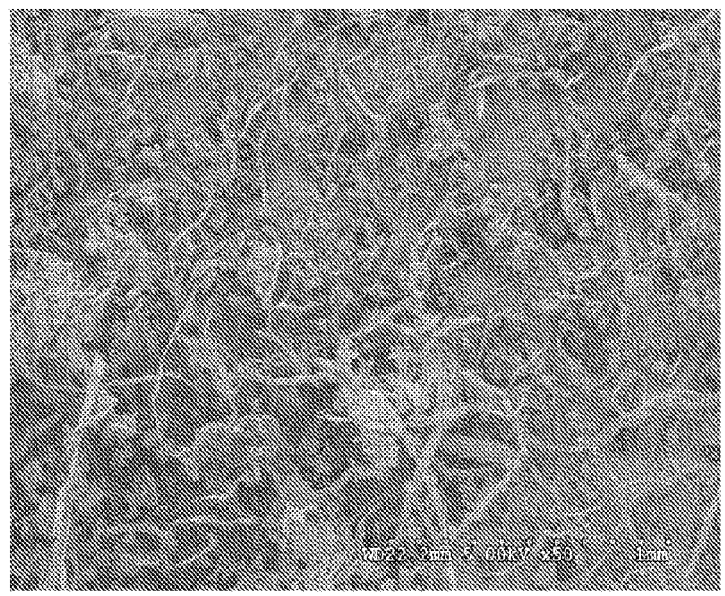
FIG. 1 is a scanning electron microscope (SEM) image of the hydrochar prepared in Example 1. The image was obtained employing an accelerating voltage of 5 kV and a magnification of 100. Size dimensions between individual dots on the 500 μm scale are 50 This image is consistent with the more macroscopic appearance of the hydrochar, as resembling a felt-like material. The fibrous material present in the hydrochar is believed to be cellulose that is resistant to HTC conditions of this invention. Water-insoluble phosphate salts become agglomerated and are either physically trapped within or adhered to the cellulosic fibrous network.

Hydrothermal carbonization (HTC; also referred to as Thermal Hydrolysis in the waste processing industry) is a process in which biomass, soluble or insoluble, is heated in water in a confined system at temperatures and times depending on the biomass substrate. With lignocellulosic materials, temperatures of 170 to 300° C. and reaction times of 4 to 16 hours are employed. Cellulose is a very recalcitrant biopolymer that requires the relatively high temperatures and long reaction times. With essentially non-cellulosic biomass materials such as microalgae and relatively low cellulose-containing biomaterials such as fermentation residues, reaction conditions are less severe, with temperatures ranging from 180 to 225° C. and times from 0.25 to 2 hours. With both lignocellulosic and low cellulosic materials, the process can result in formation of an insoluble hydrochar that is carbonized, i.e., its % carbon is increased relative to starting material, and its mass reduced, i.e., a densification. Thermal processing of municipal wastes has been conducted from 130 to 170° C. and for periods of less than 1 hour. An expressed purpose of this procedure was to pre-treat sludges to provide an improved feedstock (relative to untreated waste) for anaerobic digestion and microbial conversion into methane gas in a time efficient manner. Therefore, the objective was not to provide a highly carbonized hydrochar product but one that is dewatered, i.e., densified, and a significant portion of the carbon in the waste materials converted into water soluble organic compounds that are more readily accessible to microbial attack. A surprising aspect of thermal hydrolysis of sewages is that hydrochar products generally contain a majority of the phosphorus present in the system, whereas with microalgae and fermentation residues the phosphorus was essentially completely contained within the aqueous suspending medium as a water soluble phosphate product. Phosphorus recovery is not an issue with lignocellulosic materials, as they generally contain very low quantities of phosphorus.

Phosphorus has been recovered from sewage wastes employing a process referred to as the Krepro or Cambi/Krepro process [Karlsson, I. (2001) Full scale plant recovering iron phosphate at Helsingborg, Sweden. Proc. 2nd Int. Conf. on Recovery of Phosphates from Sewage and Agricultural Waste, CEEP, Holland, 12-14 Mar. 2001]. In this process, the sludge waste material is thickened to 5 to 7% solids, acidified with sulfuric acid to pH 1 to 3, thermally hydrolyzed at 140° C. for 30 to 40 minutes, centrifuged to remove fines (hydrochar), and the phosphates precipitated as ferric phosphate by addition of ferric sulfate to the centrate. Hydrochars were dewatered in the process to about 50% dry solids and were described as having high energy contents, equal to that of wood chips. Ferric phosphate could be employed directly onto agricultural fields as a fertilizer. A significant disadvantage of the Krepro process is the acidification step with sulfuric acid designed to solubilize the phosphate (and any heavy metals present in the system) and position them in the centrate. Strong acids are not compatible with stainless steel equipment that is the work horse construction material of the chemical reactor industry. Special and expensive alloys and metals such as Hasteloy are required for this corrosive reaction mixture, and, while iron is an essential element that is applied with the ferric phosphate product, too much iron can lead to acidification and deterioration of agricultural soils. The pre-treatment concentration step also requires extra process steps and probable use of expensive chemical flocculating additives.

Briefly, methods disclosed herein can provide a process that can transform municipal and agricultural sewages from materials having very little or negative commercial value into materials having significant economic value with significantly less negative environmental impact. An exemplary method as disclosed herein includes the steps of a) optionally, adding a multivalent cationic metal salt to a wet sewage material; b) subjecting the sewage in its native wet state, optionally with some added water, to hydrothermal carbonization to create a hydrochar and aqueous product stream; c) isolating the hydrochar from the aqueous product stream; d) optionally, extracting fatty acids and derivatives that are sorbed onto the hydrochar using an organic solvent; e) treating the optionally solvent extracted hydrochar with aqueous acid to release and dissolve phosphate and heavy metal ions from the hydrochar; f) isolating the optionally solvent and acid extracted hydrochar from the acidic aqueous product stream; g) optionally, subject the acidic aqueous product stream to heavy metal separation methods; and h) removing or concentrating water from the acidic aqueous product stream to obtain phosphoric acid and derivatives thereof.

Useful sewage sludges in the process include human wastes such as primary sludges, activated wastes, digested sludges and the like; dairy cattle manures (e.g., from calves, heifers, both dry and lactating cows and the like); beef cattle manures (e.g., from calves, high forage and high energy cattle and the like); swine manures (e.g., from boars and growing, finishing, gestating, and lactating sows and the like); poultry manures (e.g., from laying and broiler chickens, turkeys, ducks and the like); and horse manures. Preferably, the sewage sludges are utilized as received with no additional water or any catalyst added before HTC. Preferred manures are human primary sludges that generally contain 2 to 5% dry solids and swine sludges from lagoons associated with CAFOs that range in solids content from 2 to 6% by weight. With some manures and sludges such as poultry additional water may be required for effective transfer into the HTC reactor and for sufficient water to be present for hydrothermal reactions. While not wishing to be bound by any mechanistic interpretation, it is believed that the presence of multivalent metal cations such as aluminum, iron, zinc, magnesium, and calcium form insoluble phosphate salts in the milieu that become agglomerated and can become trapped within or attached to inert material such as cellulose fibers in the sewage or manure. With human sewages, for example, sufficient metal ions are present to bind or sorb essentially all of the phosphate present in the system. On the other hand, with swine manures addition of small amounts of multivalent metal cationic salts can result in total phosphate binding, whereas in their absence only about half of the phosphate is bound. Therefore, considerable control in terms of level of phosphorus binding can be exercised using the process.

Useful multivalent cationic materials can form phosphate salts having a solubility product constant (Ksp) of less than $10^{-5}$ in water at 25° C. In some embodiments the phosphate salts have a Ksp less than $10^{-8}$, in certain embodiments less than $10^{-15}$, and in other certain embodiments less than $10^{-35}$. Sulfates, nitrates, and chlorides of aluminum, calcium, iron (III), magnesium and zinc can be suitable soluble salt additives in the process. Aluminum is the most common metal present in the earth's crust and one possessing a stable oxidation state of +3 and is preferred. Concentrations employed are relatively low at 0.1 to 10%; preferably 1.0 to 7.5%; and most preferably 2.0 to 5.0% based on total dry solids in the sewage. Insoluble phosphate salts created on addition of these multivalent cationic materials are believed to be bound onto insoluble materials, e.g., cellulose, present in the system and adhered thereto through a binding event associated with even moderate degrees of carbonization, i.e., increased % C values relative to starting sewage material, are believed to function as a binding agent to adhere the particles to insoluble materials present in the system.

HTC reactions can be accomplished in preferably stainless steel reactors that feature batch, continuous or a combination of batch and continuous processing methods. Conditions for HTC range from 185 to 225° C.; preferably 200 to 220° C. and more preferably 200 to 210° C. for period ranging from 0.25 to 2.0 hours; preferably 0.25 to 1 hour; and more preferably 0.25 to 0.5 hour. Corresponding reaction pressures are essentially those of the vapor pressure of water alone, e.g., 10 to 26 atmospheres, at the respective temperatures, as very few gaseous products are generated within these temperature ranges. Concentrations of sewages and manures (based on a dry solids) range from as low as 0.25% to 30%; preferably 1 to 20%; and more preferably 3 to 15% solids. Isolation of the hydrochar from the aqueous product stream can be accomplished by filtration, centrifugation, or a combination thereof, and preferably by filtration.

It is also anticipated that the process could be modified at this point such that the isolated hydrochar, especially as a carbon-neutral fuel, could, with accompanying sorbed fatty acids and bound phosphates and heavy metals, be subjected to combustion. The remaining residue or ash would contain more highly concentrated levels of phosphate and heavy metals. The ash could be treated with acid to recover phosphate and usable heavy metals, much in the manner described further on in the disclosure of the process of this invention.

Extraction of the fatty acids and derivatives from the hydrochar can be conducted using an organic solvent, and since these compounds are sorbed essentially onto the surface of the hydrochar, relatively brief, e.g., a few minutes, of well agitated exposure of the organic solvent and hydrochar can be sufficient. Suitable organic solvents include ethers such as ethyl ether and methyl t-butyl ether; ester solvents such as ethyl and methyl acetate; ketone solvents such as acetone and methyl ethyl ketone; and hydrocarbon solvents such as hexane and heptanes. Because the hydrochars contain some moisture, e.g., approximately 50%, preferred extraction solvents include acetone and methyl t-butyl ether, as these solvents also can dissolve small amounts of water present and remove it as well as the fatty acids and derivatives from the hydrochar. Extraction of the fatty acids and derivatives is optional because in some embodiments the quantity of these materials may be too small for economic recovery, and if combustion of the hydrochar is ultimately intended, these materials can facilitate pelletizing the hydrochar as well as add substantially to the heat content.

Acids suitable to treat the hydrochar are strong inorganic acids such as sulfuric, hydrochloric and nitric acids, with sulfuric and hydrochloric being preferred. Treatment generally involves employment of an acid solution with concentrations from 0.1 to 1.5 N and isolating the acid-treated hydrochar and acidified filtrate from the heterogeneous mixture. Since the interaction of the acid with the hydrochar is one of ion exchange, i.e., exchange of a proton for multivalent metal cations to form phosphoric acid, and such exchange interactions take place very rapidly, treatment times can be only a few minutes and conducted at room temperature. Isolation of the optionally solvent and acid extracted hydrochar from the acidic aqueous extract can be conducted using filtration, centrifugation, or a combination thereof, with filtration being preferred.

In certain embodiments it may be desirable to leave heavy metal salts in the acidified aqueous extract. Elements such as copper and zinc that are the primary multivalent metal cations present in many agricultural manures, and metal salts of these elements in moderate levels may be desirable in a fertilizer preparation. Elements such as nickel, chromium, cadmium, mercury, and lead that are common in municipal waste sludges, are less agronomically desirable; however they are valuable materials in their neutral metal state. These multivalent metal cations can be separated, along with copper and zinc, by addition of sodium sulfide to the extract. Corresponding sulfide salts of these metals are very insoluble and can be removed from the system by filtration or centrifugation for further processing. Alternatively, cationic ion exchange resins can be utilized to remove multivalent cations from the extract, and the multivalent cations can subsequently be released from the ion exchange material by treatment with aqueous acid.

Concentration of the aqueous acidified phosphate extract solution can be conducted by evaporation or distillation of water from the solution. Alternatively, membrane removal methods such as cross-flow filtration or dialysis separation methods known in the art can be employed. If conversion of phosphoric acid into polyphosphoric acids is desired, heating the concentrated phosphoric acid solution at reduced atmospheric pressure can be employed.

Figure 2:
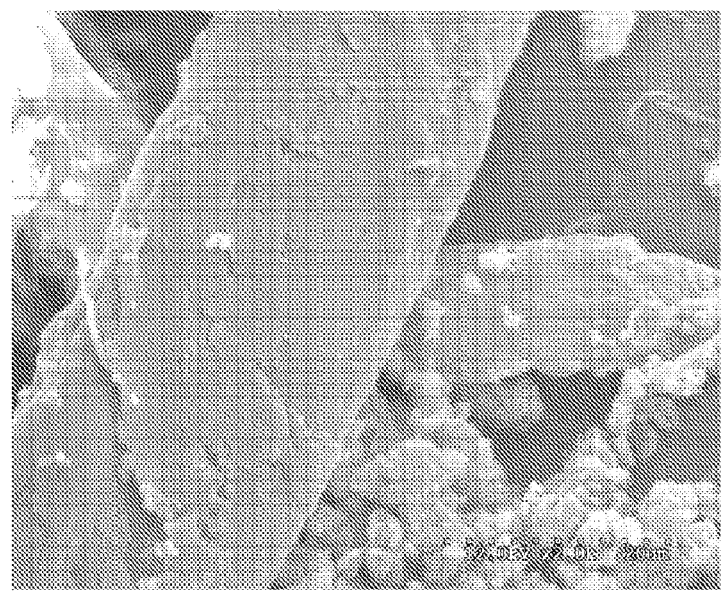
FIG. 2 is a SEM image of the same material in FIG. 1, only at higher magnification (2000, with a 12 kV accelerating voltage). This image provides additional support for the insoluble particles being agglomerated and actually adhered to the fibrous strands.

The exact mechanism of phosphate binding is presently unknown, and, while not wishing to be bound by any explanation, the following hypothesis is offered and supported to a degree by the images and graphical information in the drawings. Clearly, soluble phosphate anions would become insoluble in the presence of multivalent metal cations such as aluminum, iron, magnesium, calcium and zinc whose corresponding phosphate salts have Ksp values less than $10^{-5}$. HTC reactions are believed to occur, especially with insoluble biomass substrates such as solid sewages, by initial hydration of polysaccharides present to form soluble carbohydrate species. Dehydration can occur in these carbohydrate derivatives both intramolecularly for increased carbon content (carbonization) and intermolecularly to build hydrochar mass. Eventually, polymerization and precipitation will occur, with nucleation being promoted by insoluble phosphate present in the reaction milieu Proteins and hydrolyzed derivatives thereof also can become involved in formation of the hydrochar with carbohydrates via a cascade of reactions known as the Maillard reaction. Growing organic material can also collect on insoluble cellulose surfaces, ultimately providing for binding of the two insoluble materials together. Despite the level of carbonization being typically quite low, especially with municipal sewage wastes, the level may be sufficient for this binding to occur. This is supported by SEM of FIG. 2, in which insoluble phosphate salt aggregates appear to be attached to fibrous material. Acidification of the hydrochar causes hydrogen ions to displace multivalent metal cations.

The present invention provides a realistic approach that can address the looming global problem of phosphate scarcity and potential insufficient food production in future generations. The method can effectively capture and sequester phosphorus in a form (phosphoric acid and derivatives) that provides for storage of fertilizing materials having phosphorus pentoxide equivalents of 0.7 and greater in a volume efficient manner. The method can also provide for control of the amount of phosphorus sequestered in certain sewages, e.g., swine sewages, in which HTC does not result in binding all the phosphate present in the system on the hydrochar. In certain embodiments, a method in which only a portion, e.g., half, of the phosphate present is bound is desirable, and the aqueous product stream having only a portion of the original phosphate but with substantial potassium and nitrogen contents can be employed onto agricultural soils directly as a fertilizer. In this manner, quantities of phosphate applied to soils can be reduced to satisfy environmental concerns, while still providing adequate levels to growing plants. The process can also provide for extraction of fatty acids and derivatives that are created by hydrolysis of triacylglycerides and other fatty acid ester compounds such as phospholipids during HTC. Fatty acids do not chemically contribute to hydrochar formation but are bound or sorbed onto the hydrochar, from which they can be removed and isolated by extraction using an organic solvent. Fatty acids can be employed directly for conversion into renewable liquid transportation fuels such as gasoline, diesel fuel, aviation fuel, and biodiesel. Alternatively, they can be used in the manufacture of soaps, cosmetics, and transformer oils. Extracted hydrochars can be utilized as high heat content, carbon-neutral fuel supplements to coal, thereby reducing the carbon footprint in the generation of electricity. Alternatively, due to their low ash contents, hydrochars can be used as pro-products and carbon sources to produce synthesis gas (CO and $H_2$) for manufacture of industrial chemicals and liquid transportation fuels via Fischer-Tropsch, or as a reductant and replacement for coal coke in steel manufacture. Still other applications for the extracted hydrochar derive from their relatively amphiphilic nature. Hydrochars possess relatively hydrophobic particle interiors due to aromatization and production of furans and benzenoid structures, but the particles also have surfaces containing relatively high concentrations of hydrophilic groups such as carboxyl, hydroxyl, and carbonyl that provide for wetting in water and other specific interactions such as ion exchange to remove cationic solutes from industrial waste waters. The process can further provide sterile, pathogen-free, deodorized aqueous product streams that can be employed directly as fertilizers in certain embodiments or subjected to anaerobic digestion to obtain methane as another energy product. The process can still further provide for the recovery of heavy metals from the acidified extract of the hydrochar. These heavy metals can be reduced to electrically neutral metals that have utilities such as catalysts or as components of metallic alloys to provide specific properties such as increased strength, corrosion resistance, and reduced densities.

Figure 4:
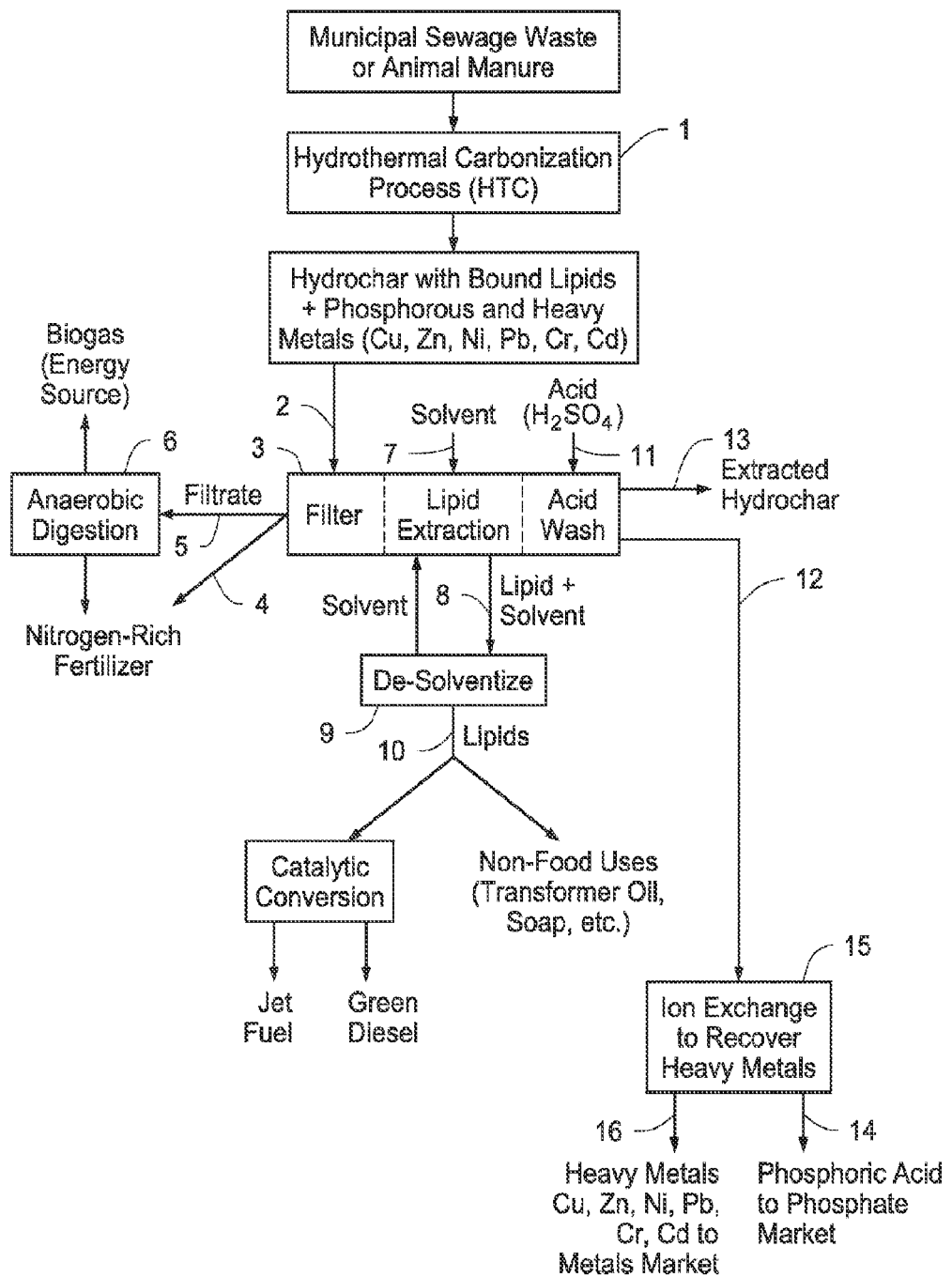
FIG. 4 illustrates a schematic flow chart for a hydrothermal carbonization process for sewage waste and animal manure.

An exemplary schematic flow chart for a hydrothermal carbonization process for sewage waste and animal manure is illustrated in FIG. 4. The municipal sewage waste or animal manure either in its original wet state or altered by addition of water and optional addition of a multivalent cationic salt as described in the specification is conveyed into the hydrothermal carbonization reactor 1, which can be a batch reactor, a continuous reaction system, or a combination of the two. After the HTC reaction has been completed, the reaction products, hydrochar and aqueous product stream can be conveyed through pipe 2 into a separation unit 3, which can be, for example, a filter or centrifuge to separate hydrochar from the aqueous product stream. In preferred embodiments, a decanter-type apparatus is used and illustrated that employs both direct filtration and centrifugation principles. In the initial filter phase, hydrochar and aqueous product stream can be separated, and the aqueous product stream can be removed as filtrate through pipes 4 or 5 to be utilized as a nitrogen-rich, phosphate-depleted fertilizer and/or subjected to anaerobic digestion in unit 6 to produce biogas. The filtered hydrochar can then be moved using, for example, an auger system as illustrated from left to right in unit 3. The filtered hydrochar can then be subjected to extraction using an organic solvent introduced through pipe 7, with the extract removed through pipe 8 and conveyed into a solvent removal and recycle unit 9. The lipids (fatty acids) that are obtained as a slightly viscous liquid can be removed through pipe 10. In one embodiment, the lipids can be processed and used in non-food applications such as, for example, soaps, transformer oils, etc. In another embodiment, the lipids can be subjected to catalytic conversion by known techniques into, for example, jet fuel, green diesel, and other fuels. After solvent extraction in separation unit 3, the solvent-extracted hydrochar can be conveyed into the acid wash section of unit 3. Acid can be introduced through pipe 11, the acidic extract can be removed through pipe 12 and the solvent- and acid-extracted hydrochar can be obtained as a slightly moist granular solid from pipe 13. The acid extract can be subjected to ion exchange in unit 15, with heavy metal and multivalent cationic materials being withheld on the cation exchange resin in unit 15. The phosphoric acid diluted with water can be obtained through pipe 14. Water can subsequently be removed by methods described herein, with more concentrated phosphoric acid and corresponding derivatives thus obtained. Heavy metal and multivalent cationic salts can be subsequently obtained by treating the ion exchange resin containing these cations with acid and separation through pipe 16.

The following examples are offered to further illustrate various specific embodiments and techniques of the present disclosure. It should be understood, however, that many variations and modifications understood by those of ordinary skill in the art may be made while remaining within the scope of the present disclosure. Therefore, the scope of the disclosure is not intended to be limited by the following examples. It is to be understood that the particular examples, materials, amounts, and procedures are to be interpreted broadly in accordance with the scope and spirit of the invention as set forth herein.

EXAMPLES

Elemental analyses, heats of combustion and ash contents were determined at Galbraith Laboratories, Inc. (Knoxville, Tenn.), Huffman Laboratories, Inc., (Golden, Colo.), and the Soil Sciences Department of the University of Minnesota (St. Paul, Minn.). Inductively coupled plasma analysis was conducted at the Soil Science Department of the University of Minnesota (St. Paul, Minn.). Mixed primary/activated municipal waste sludge (28.8% dry weight) and centrates were received from the Metropolitan Council Environmental Services, Metro Plant (St. Paul, Minn.). The centrifugate sludge was stored at −16° C. and the centrate at 4° C. until use. Additional waste activated sludge (0.54% dry weight) and aerobically treated digested sludge (3.45% dry weight) were also received from the Chisago County Municipal Waste Treatment Center (Chisago City, Minn.). Swine materials were obtained either from the Department of Animal Science of the University of Minnesota (St. Paul, Minn.) or the Southern Research and Outreach Center of the University of Minnesota (Waseca, Minn.) from animals that were not fed diets containing any added phytase.

All HTC reactions were conducted in a stirred 450 mL stainless steel reactor available from Parr Instruments, Inc., (Moline, Ill.). The unit was heated to reaction temperatures using an inductively heated system provided by LC Miller, Inc. (Monterey Park, Calif.). Initially with each sewage waste material, fecal samples obtained were homogenized with water to an extent that the mixture was pourable and easily transferable into the reactor. With municipal sewage waste and swine waste, corresponding liquid portions, i.e., centrates with municipal sewage waste and urine collected separately with swine, were substituted for distilled water to provide a more realistic assessment of processing an actual waste obtained at the treatment facility or farm.

Example 1

This example provides exemplary experimental details of the HTC process and corresponding phosphorus sequestration in the hydrochar derived from municipal sewage waste. For comparison purposes, the elemental composition of starting freeze-dried municipal sewage waste was 41.57% C, 6.18% H, 5.29% N, and 2.13% P.

Frozen mixed primary and activated sludge (68.2 g at 28.8% solids containing 19.6 g of dry solids and 48.6 g of water) was placed in a Waring blender, and a total of 253.3 g of distilled water were added and blended that provided a homogeneous mixture having a pourable consistency; the % solids of the resulting slurry was 6.1%. This material was transferred into the reactor, stirred at 120 revolutions per minute (rpm), and heated to 200° C. After 2 hours the initial reactor pressure of 225 pounds per square inch (psi) had not increased and heating was discontinued. When cool, the reactor was opened and the odor of the reaction products had noticeably improved to one reminiscent of a kitchen with coffee and caramel aromas predominating. The solid hydrochar product was filtered and it was noted that the solid filtercake possessed a fibrous quality, resembling a brownish gray felt-like material in appearance. This was washed well with water and freeze-dried. The dry hydrochar weighed 11.01 g (56% mass yield). The elemental composition of the hydrochar was as follows: 45.14% C; 6.25% H; 1.79% N; and 3.01% P. The hydrochar had moderately increased levels of carbon compared to starting material and substantially reduced nitrogen content, indicating that nitrogen was largely concentrated in the filtrate (aqueous product stream). Based on the phosphorus content present in the starting material (417 mg) and that present in the hydrochar (331 mg), the amount of phosphorus sequestered was 80%.

Example 2

This example illustrates that substituting authentic centrate for distilled water in the process can provide higher mass yields of hydrochar and increased phosphorus sequestration capability. For comparison purposes, the elemental composition of the centrate was 0.14% C, 0.02% N, and 0.0118% P (hydrogen could not be determined with the aqueous solution).

The procedure of Example 1 was utilized to conduct the HTC reaction at 5.6% solids. Hydrochar was isolated in 62% yield with the following elemental composition: 42.6% C; 6.33% H; 1.63% N, and 3.32% P. The centrate (224.4 g) contributed 26 mg of P, with the starting solid sewage contributing 338 mg for a total of 364 mg of P present in the system. The amount of P sequestered in the hydrochar was 323 mg and was 89% of the P present in the original starting mixture.

Examples 3-13

A designed experiment examining HTC of municipal sewage waste in centrate was conducted based on the following input variable parameters: 1) HTC temperatures below 185° C. provided reaction mixtures that were essentially unfilterable; 2) the level of dry solids of screened primary waste sludge in municipal treatment facilities is believed to be in 3 to 5% range; and 3) and, since continuous process is ultimately desired, a reaction time of less than 2 hours was employed. Therefore, the experiments in Table 2 were conducted at reaction temperatures of 190, 200, and 210° C.; solids contents of 3, 4, and 5%; and times of 0.5, 1.25, and 2 hours.

TABLE 2

Designed Experiments Conditions and Results

| Example Number | React. Temp. (° C.) | React. Time (hours) | % Solids | Char Yield (%) | % C in Char | % P in Char | % P of Total |
|---|---|---|---|---|---|---|---|
| 3 | 190 | 0.5 | 3 | 56 | 40.7 | 3.39 | 77 |
| 4 | 190 | 0.5 | 5 | 57.5 | 42.3 | 3.22 | 69 |
| 5 | 190 | 2.0 | 3 | 55 | 39.6 | 3.92 | 84 |
| 6 | 190 | 2.0 | 5 | 51 | ND$^a$ | 3.52 | 78 |
| 7 | 200 | 1.25 | 4 | 55 | 42.0 | 3.43 | 78 |
| 8 | 200 | 1.25 | 4 | 56 | 41.3 | 3.52 | 83 |
| 9 | 200 | 1.25 | 4 | 53 | 39.3 | 3.71 | 82 |
| 10 | 210 | 0.5 | 3 | 56 | 40.7 | 3.83 | 86 |
| 11 | 210 | 0.5 | 5 | 54 | 42.0 | 3.22 | 69 |
| 12 | 210 | 2.0 | 3 | 51 | ND | 4.24 | 87 |
| 13 | 210 | 2.0 | 5 | 51 | 40.5 | 3.67 | 80 |

$^a$= ND means not determined

Standard deviations (a) for the centerpoint replicates at 200° C. were 1.1 for hydrochar yield, 1.1 for % C in char, 0.1 for % P in char, and 2.2 for % total hydrochar P of the system. Linear regression analysis equations that gave $r^2$ values greater than 0.8 were:

For System % P in the hydrochar, $r^2=0.82$:

$$Y=79.36-4.75X_1+1.75X_2+3.5X_3$$

For % P in the hydrochar, $r^2=0.92$:

$$Y=3.60-0.23X_1+0.13X_2+0.22X_3$$

wherein $X_1$=% solids, $X_2$=temperature, and $X_3$=time.

These equations indicate that greater success with phosphorus capture can be achieved at low solids, higher temperatures and longer reaction times.

Example 14

This example conducted with municipal sewage waste illustrates exemplary solvent extraction procedures that can be used to obtain fatty acid and derivative products.

The procedure of Example 1 was conducted using primary and activated waster (79.1 g at 28.8% solids containing 22.7 g of dry solids and 56.4 g of water). This material was placed in a Waring blender, and a total of 148.5 g of distilled water were added to provide a % solids level of 10.0%. This material was transferred into the reactor, stirred at 120 rpm, and heated to 200° C. for 1.25 hours. The hydrochar product was filtered and washed well with water. The gray/tan colored freeze-dried product weighed 17.2 g (76% mass yield). This material was treated with 250 mL of methyl t-butyl ether (MTBE), and the mixture was stirred magnetically for 30 minutes at room temperature. The mixture was vacuum filtered, and the filtercake washed with an additional 50 mL of MTBE. Removal of the MTBE in the extract using a rotary evaporator gave a brown oil residue weighing 3.1 g. The IR spectrum of the oil showed strong absorptions consistent with a predominant fatty acid content. The oil was submitted to Medallion Laboratories, Inc. (Minneapolis, Minn.) for fatty acid analysis and determination of a weight average molecular weight of fatty acids present; that value was 268 g/mole. Employing an NMR procedure (Heilmann, S. M., et al., Applied Energy 2011; 88(10):3286-3290, incorporated by reference) using dimethyl terephthalate as an internal standard, the % fatty acid in the sample was determined to be 63% by weight or a yield of 2.0 g or 9% of the original dry solids charged.

Examples 15-17

These Examples illustrate that other human sewage sludges can be effectively employed as substrates in the HTC process even at relatively low % solids levels for forming hydrochars with excellent phosphorus sequestering capabilities. HTC reactions were conducted at the solids received and at 200° C. for 2 hours.

TABLE 3

Examples 15-17

| Example | Sewage Sludge | % Solids | Hydrochar Yield (%) | System % P in Hydrochar |
|---|---|---|---|---|
| 15 | Activated$^a$ | 5.0 | 36 | 52 |
| 16 | Activated$^b$ | 0.54 | 32 | 72 |
| 17 | Digested$^c$ | 3.45 | 47 | 99 |

$^a$= Sample received from the Metropolitan Waste Management facility in St. Paul, MN. Freeze-dried material contained 4.27% P, with 6.35% P in hydrochar.
$^b$= Sample received from Chisago County Waste Management facility in Chisago City, MN. Freeze-dried material contained 2.64% P, with 5.78% P in hydrochar.
$^c$= Sample received from Chisago County Waste Management facility; sample contained approximately 30 ppm of a proprietary polycationic flocculating polymer additive. Freeze-dried material contained 3.26% P, with 6.92% P in hydrochar.

Examples 18-19

The following examples disclose HTC results with swine sewage materials. Analysis of starting swine feces was 45.58% C; 6.96% H; 3.12% N; and 1.53% P, and that for urine was 0.58% C; 0.35% N; and 0.0007% P. HTC reactions were conducted at 200° C., with the % solids and reaction times indicated. Swine urine by itself at 200° C. for 2 hours gave less than 0.1 g of solid material.

TABLE 4

Examples 18-19

| Example | Time (hours) | % Solids | Hydrochar Yield | % C | % H | % N | % P | System % P in Hydrochar |
|---|---|---|---|---|---|---|---|---|
| 18 (d H$_2$O) | 2 | 7.2 | 52 | 58.64 | 7.39 | 2.66 | 1.62 | 55 |
| 19 (urine) | 0.5 | 5.6 | 43 | 51.34 | 7.16 | 2.18 | 2.46 | 69 |

These examples show that at least a portion of the phosphorus present in the sample can be sequestered, leaving a portion in the aqueous product stream for possible use as a reduced-phosphate, lower odor fertilizer. The % C value of the hydrochar in Example 18 is also noteworthy, as that hydrochar with 58.5% would possess a relatively high energy content, carbon neutral fuel and one substantially higher than wood chips.

Example 20

This example illustrates that phosphorus can be recovered in the form of phosphate from a hydrochar by treatment with aqueous acid.

To 5.10 g of the hydrochar obtained in Example 1 were added 100 mL of 0.1 N HCl, and the mixture was stirred magnetically at room temperature for 30 minutes. The mixture was filtered and the acid-treated hydrochar was washed with distilled water until the washings were neutral. The hydrochar was freeze-dried and analyzed for % P. The starting hydrochar having a % P level of 3.01% after acid wash contained 0.85% P which is a reduction of 72%.

Example 21

This example shows that heavy metals and multi-metal cationic phosphates are concentrated, relative to the starting sewage, in the hydrochar. Heavy metal cations can be isolated from hydrochars and processed into neutral metals having utility. Multimetal cations present and concentrated in the hydrochar also provide mechanistic insight.

Freeze-dried mixed primary/activated municipal waste and corresponding hydrochar from Example 1 were digested in nitric acid and heated until complete solution of solids was achieved. These solutions were then examined for metal content using inductively coupled plasma analysis.

TABLE 5

Multivalent Metal Analysis (in ppm)

| | Material | | | | |
|---|---|---|---|---|---|
| | Mg | Zn | Ca | Fe | Al |
| Starting | 5203 | 419 | 18484 | 6550 | 4272 |
| Hydrochar | 2229 | 410 | 8082 | 5804 | 3601 |

Figure 3:
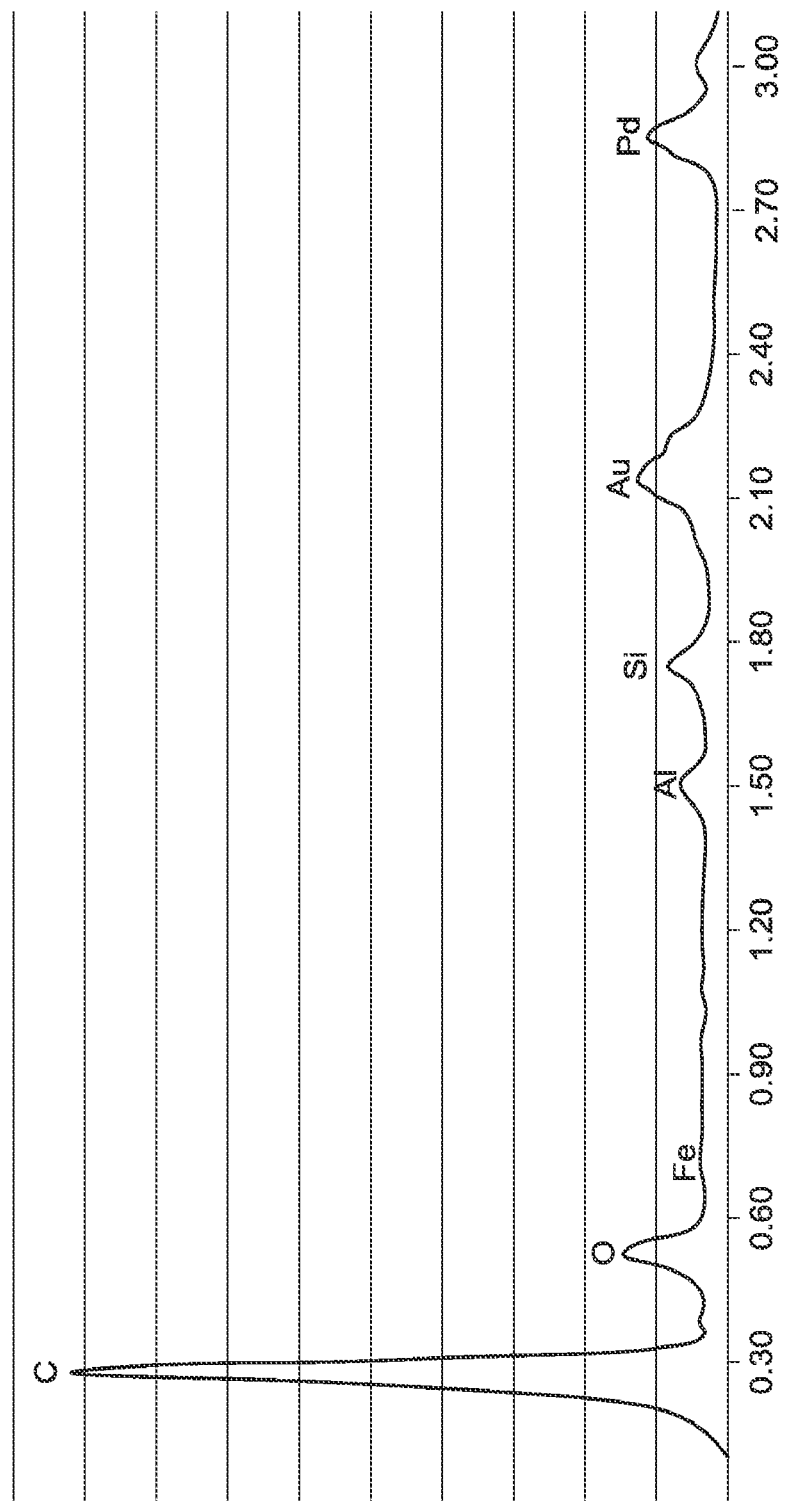
FIG. 3 is a graphical depiction of an energy-dispersive spectroscopy (EDS) analysis of the fibers of Example 1 to include particulate material adhered thereto. This technique allows for specific elemental analysis of components within a SEM image. Elements identified on the fibrous strands are aluminum, silicon and traces of iron. Gold and palladium are extraneous as they are introduced in the EDS procedure.

The above data indicate that increased levels of iron and aluminum remain in the hydrochar compared to the others with 88% and 84% of those elements present in the starting fecal material remaining in the hydrochar. These results confirm the elemental analysis results of the EDS analysis in FIG. 3.

TABLE 6

Heavy Metal Analysis (in ppm)

| | Material | | | |
|---|---|---|---|---|
| | Ni | Pb | Cd | Cr |
| Starting | 27 | 14 | 4 | 6 |
| Hydrochar | 43 | 38 | 18 | 95 |

Since the mass yield of hydrochar in Example 1 was 56%, virtual doubling of the starting concentration of each heavy metal indicated almost quantitative containment of these heavy metals within the hydrochar.

Example 22

This example illustrates that phosphate binding in hydrochars can be increased when a multivalent metal cationic salt is added. Swine manure from the University of Minnesota Southern Research and Outreach Center (Waseca, Minn.) was subjected to hydrothermal carbonization conditions of 200° C., 1.25 hours, and at 6.9% solids in distilled water. When cool, the reaction mixture was filtered and the filtrate analyzed for phosphate concentration using a BioVision Phosphate Assay Kit (Catalog #410-500; Mountainview, Calif.), with the result being 83 mM of phosphate being determined.

When the same experiment was duplicated except in the presence of 5000 ppm $Fe^{+3}$ (as $FeCl_3$), the filtrate phosphate concentration was 32 mM, a reduction of 62% in phosphate concentration.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of obtaining a phosphate from a sewage material, the method comprising:
    subjecting a wet sewage material to a hydrothermal carbonization process to produce a hydrochar and an aqueous product stream;
    isolating the hydrochar from the aqueous product stream;
    treating at least a portion of the isolated hydrochar with an aqueous acid under conditions effective to provide an aqueous phosphate material; and
    isolating the acid-treated hydrochar from the aqueous phosphate material.

2. The method of claim 1 wherein the aqueous phosphate material is suitable for use as a fertilizer, or as a feedstock for anaerobic digestion without further processing.

3. The method of claim 1 wherein the aqueous phosphate material includes heavy metals, and the method further comprises removing at least a portion of the heavy metals from the aqueous phosphate material.

4. The method of claim 1 further comprising removing at least a portion of the water from the aqueous phosphate material to provide a dewatered phosphate material.

5. The method of claim 4 wherein removing at least a portion of the water comprises a process selected from the group consisting of evaporation, distillation, membrane removal, and combinations thereof.

6. The method of claim 5 wherein the membrane removal process comprises crossflow filtration or dialysis separation.

7. The method of claim 4 wherein the dewatered phosphate material is suitable for use without further processing as a fertilizer.

8. The method of claim 1 wherein the wet sewage material comprises one or more materials selected from the group consisting of human wastes, dairy cattle manures, beef cattle manures, swine manures, poultry manures, and horse manures.

9. The method of claim 1 wherein water is added to the wet sewage material to adjust the solids content.

10. The method of claim 1 wherein the wet sewage material has a solids content of 0.25% to 30% by weight.

11. The method of claim 1 wherein the wet sewage material has a cellulose content of less than 50% by weight.

12. The method of claim 1 wherein at least one multivalent cation is added to the wet sewage material.

13. The method of claim 12 wherein the at least one multivalent cation forms a phosphate salt having a solubility product constant (Ksp) of less than $10^{-5}$.

14. The method of claim 12 wherein the at least one multivalent cation forms a phosphate salt having a solubility product constant (Ksp) of less than $10^{-8}$.

15. The method of claim 12 wherein the at least one multivalent cation forms a phosphate salt having a solubility product constant (Ksp) of less than $10^{-5}$.

16. The method of claim 12 wherein the at least one multivalent cation forms a phosphate salt having a solubility product constant (Ksp) of less than $10^{-35}$.

17. The method of claim 12 wherein 0.1% to 10% by weight of the at least one multivalent cation is added to the wet sewage material, based on the total dry solids of the sewage material.

18. The method of claim 12 wherein the at least one multivalent cation is selected from the group consisting of Al, Ca, Mg, Fe, Zn, and combinations thereof.

19. The method of claim 1 wherein the temperature of the hydrothermal carbonization process is 185° C. to 225° C.

20. The method of claim 1 wherein the time of the hydrothermal carbonization process is 0.25 hours to 2 hours.

21. The method of claim 1 wherein the pressure of the hydrothermal carbonization process is 10 to 26 atmospheres.

22. The method of claim 1 wherein the initial pH of the wet sewage material in the hydrothermal carbonization process is 4 to 8.

23. The method of claim 1 wherein isolating the hydrochar from the aqueous product stream comprises filtration, centrifugation, or a combination thereof.

24. The method of claim 1 wherein the aqueous product stream is suitable for use as a fertilizer or an anaerobic digestion substrate without further processing.

25. The method of claim 1 wherein isolating the acid-treated hydrochar and/or acid and organic solvent-treated hydrochar from the aqueous phosphate material comprises filtration, centrifugation, or a combination thereof.

26. The method of claim 1 wherein untreated and/or treated hydrochar is suitable for use directly as carbon-neutral energy products.

27. The method of claim 1 wherein the wet sewage material is untreated.

28. The method of claim 1 further comprising combusting at least a portion of the isolated hydrochar and/or the isolated organic solvent-treated hydrochar to form an ash.

29. The method of claim 28 further comprising treating at least a portion of the ash with an aqueous acid under conditions effective to provide an aqueous phosphate material and/or heavy metals.

30. A method of obtaining a phosphate from a sewage material, the method comprising:
   subjecting a wet sewage material to a hydrothermal carbonization process at a temperature of 185° C. to 225° C. and a pressure of 10 to 26 atmospheres to produce a hydrochar and an aqueous product stream;
   isolating the hydrochar from the aqueous product stream using filtration and/or centrifugation;
   treating at least a portion of the isolated hydrochar with an aqueous acid under conditions effective to provide an aqueous phosphate material; and
   isolating the acid-treated hydrochar from the aqueous phosphate material using filtration and/or centrifugation.

31. The method of claim 30 further comprising removing at least a portion of the water from the aqueous phosphate material to provide a dewatered phosphate material.

32. The method of claim 31 wherein removing at least a portion of the water comprises a process selected from the group consisting of evaporation, distillation, membrane removal, and combinations thereof.

33. The method of claim 32 wherein the membrane removal process comprises crossflow filtration or dialysis separation.

* * * * *